(12) United States Patent
Li et al.

(10) Patent No.: US 11,193,927 B2
(45) Date of Patent: Dec. 7, 2021

(54) AUTOMATED BODY FLUID ANALYSIS

(71) Applicant: Abbott Laboratories, Abbott Park, IL (US)

(72) Inventors: Wenjing Li, Sunnyvale, CA (US); Emily H. Lin, Cupertino, CA (US); Jiong Wu, Los Gatos, CA (US)

(73) Assignee: Abbott Laboratories, Abbott Park, IL (US)

( * ) Notice: Subject to any disclaimer, the term of this patent is extended or adjusted under 35 U.S.C. 154(b) by 290 days.

(21) Appl. No.: 16/330,289

(22) PCT Filed: Sep. 7, 2017

(86) PCT No.: PCT/US2017/050537
§ 371 (c)(1),
(2) Date: Mar. 4, 2019

(87) PCT Pub. No.: WO2018/049064
PCT Pub. Date: Mar. 15, 2018

(65) Prior Publication Data
US 2019/0204301 A1 Jul. 4, 2019

Related U.S. Application Data

(60) Provisional application No. 62/385,055, filed on Sep. 8, 2016.

(51) Int. Cl.
*G01N 33/52* (2006.01)
*G01N 33/50* (2006.01)
(52) U.S. Cl.
CPC ..... *G01N 33/5094* (2013.01); *G01N 33/5002* (2013.01); *G01N 33/52* (2013.01)

(58) Field of Classification Search
CPC ........... G01N 33/5094; G01N 33/5002; G01N 33/52; G01N 2015/1488; G01N 15/1459;
(Continued)

(56) References Cited

U.S. PATENT DOCUMENTS 5,361,165 A 11/1994 Stringfellow et al.
8,148,101 B2 4/2012 Kim et al.
(Continued)

FOREIGN PATENT DOCUMENTS

JP 2014520253 8/2014
WO WO2006/080239 8/2006
(Continued)

OTHER PUBLICATIONS

Cheng (1995) "Mean Shift, Mode Seeking, and Clustering", IEEE Transactions on Pattern Analysis and Machine Intelligence 17(8): 790-799.
(Continued)

*Primary Examiner* — Jennifer Wecker
*Assistant Examiner* — Michael Paul Shimek
(74) *Attorney, Agent, or Firm* — Edward J. Baba; Mandar A. Joshi; Bozicevic, Field & Francis LLP

(57) ABSTRACT

Methods, devices, and systems for automated cellular analysis of a body fluid sample are disclosed. The methods, devices, and systems apply watershed transform to data, generated by flowing a body fluid sample through a flow cytometer, to determine threshold(s) to be used for analysis of the data.

34 Claims, 8 Drawing Sheets

(58) Field of Classification Search
CPC .... G01N 2015/1402; G01N 2015/1006; G06T 2207/10056; G06T 2207/20152; G06T 2207/30024; G06T 7/155; G06T 7/136; G06T 7/11; G06K 9/0014; G06K 9/342; G06K 9/00147
See application file for complete search history.

(56) References Cited

U.S. PATENT DOCUMENTS

| | | | |
|---|---|---|---|
| 8,911,669 | B2 | 12/2014 | Krockenberger et al. |
| 2004/0241769 | A1* | 12/2004 | Crews ............... G01N 15/1456 435/7.21 |
| 2007/0211928 | A1* | 9/2007 | Weng .................. G06T 7/0012 382/128 |
| 2008/0113317 | A1 | 5/2008 | Kemp et al. |
| 2008/0267497 | A1 | 10/2008 | Fan |
| 2008/0280777 | A1* | 11/2008 | Bittner ..................... G16B 5/00 506/9 |
| 2010/0008576 | A1 | 1/2010 | Piramuthu |
| 2011/0178716 | A1* | 7/2011 | Krockenberger .. G01N 33/4915 702/19 |
| 2013/0164740 | A1 | 6/2013 | Wu et al. |
| 2013/0230230 | A1 | 9/2013 | Ajemba et al. |

FOREIGN PATENT DOCUMENTS

| | | |
|---|---|---|
| WO | WO2015/157369 | 10/2015 |
| WO | WO2016/001223 | 1/2016 |

OTHER PUBLICATIONS

Kanungo, et al. (2002) "An Efficient κ-Means Clustering Algorithm: Analysis and Implementation", IEEE Transactions on Pattern Analysis and Machine Intelligence 24(7): 881-892.

Kim, et al. (2003) "Automated Red Blood Cell Differential Analysis on a Multi-Angle Light Scatter/Fluorescence Hematology Analyzer", Cytometry Part B (Clinical Cytometry), 56B: 43-54.

Vincent, et al. (1991) "Watersheds in digital spaces: an efficient algorithm based on immersion simulations." IEEE Transactions on Pattern Analysis and Machine Intelligence 13(6): 583-598.

Andreatta, Stefan, et al., "Detection of Subgroups From Flow Cytometry Measurements of Heterotrophic Bacterioplankton by Image Analysis", Cytometry 44, 2001, 218-225.

Bashashati, Ali, et al., "A Survey of Flow Cytometry Data Analysis Methods", Advances in Bioinformatics 2009, 2009, 1-19.

Kent, David, et al., "Isolation and Assessment of Long-Term Reconstituting Hematopoietic Stem Cells from Adult Mouse Bone Marrow", Current Protocols in Stem Cell Biology 2A(3), 2007, 4.1-4.23.

Koyuncu, Can Fehrettin, et al., "Iterative H-Minima-Based Marker-Cotrolled Watershed for Cell Nucleus Segmentation", Cytometry Part A 89A, 2016, 338-349.

Ljosa, Vebjorn, et al., "Introduction to the Quantitative Analysis of Two-Dimensional Fluorescense Microscopy Images for Cell-Based Screening", PLOS Computational Biology 5(12), 2009, e10000603, 10 pages.

Mancas, Matei, et al., "Towards an automatic tumor segmentation using iterative watersheds", SPIE—International Society for Optical Engineering Proceedings 5370, 2004, 1598-1608.

Rodrigues, M. A., et al., "Optimized Automated Data Analysis for the CytoKinesis-Block Micronucleus Assay Using Imaging Flow Cytometry for High Throughput Radiation Biodosimetry", Cytometry Part A 89A, 2016, 653-662.

Sri Nagesh, A., et al., "An Improved Iterative Watershed and Morphological Transformation Techniques for Segmentation of Microarray Images", IJCA Special Issue on CASCT, 2010, 77-87.

Wahlby, C., et al., "Combining intensity, edge and shape information for 2D and 3D segmentation of cell nuclei in tissue sections", Journal of Microscopy 215(Pt 1), 2004, 67-76.

* cited by examiner

WBC
y = 0.8879x + 7.6279
R² = 0.91

PMN%
y = 0.9222x - 2.229
R² = 0.875

RBC
y = 0.8684x - 159.37
R² = 0.9821

MN%
y = 0.9222x + 10.006
R² = 0.875

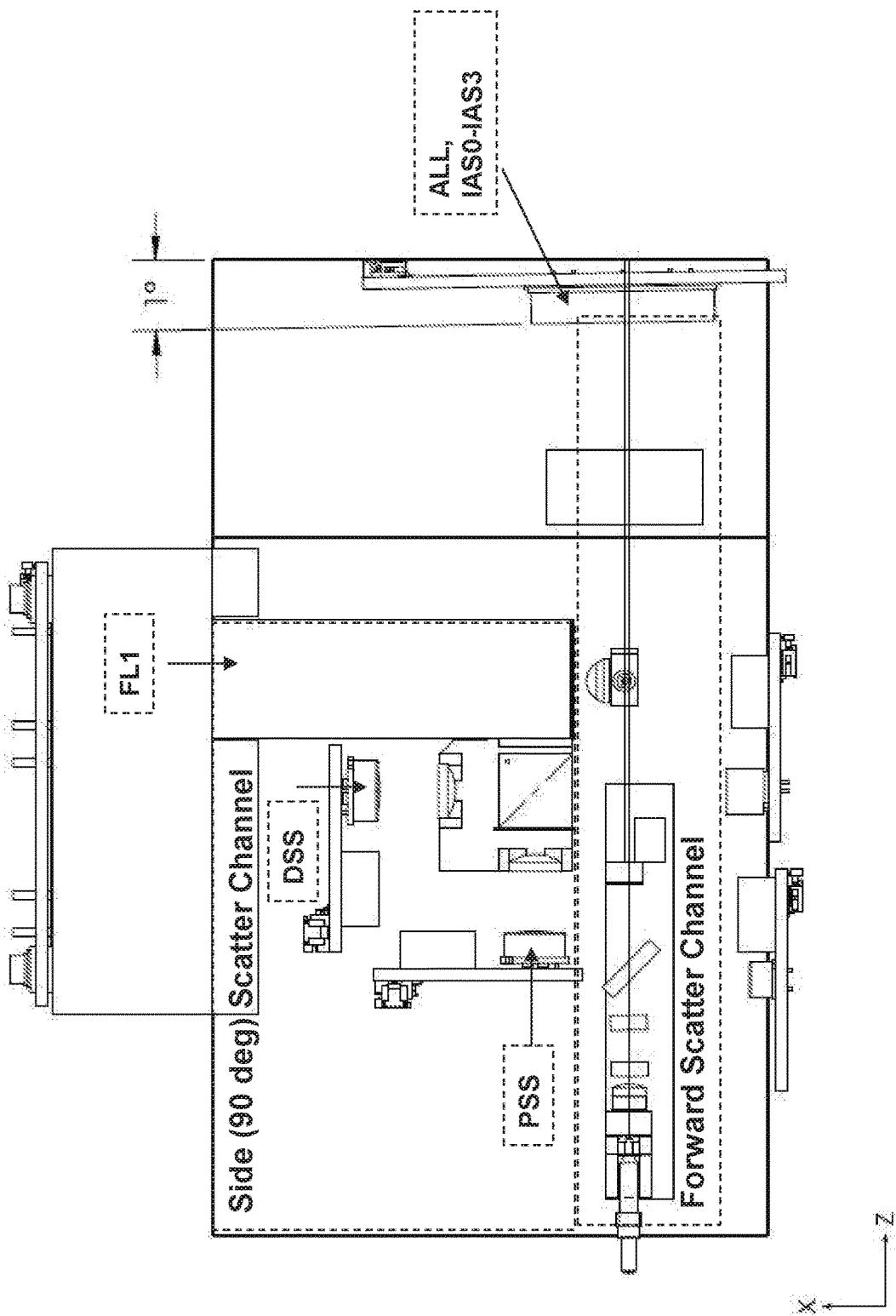

AUTOMATED BODY FLUID ANALYSIS

CROSS-REFERENCE TO RELATED APPLICATIONS

This application claims the benefit of U.S. Provisional Patent Application No. 62/385,055 filed Sep. 8, 2016, which application is incorporated herein by reference in its entirety.

BACKGROUND

Analysis of body fluids provides important information regarding composition of the body fluid including types of cells, enumeration of the different types of cells, presence of abnormal cells, presence of infectious particles (e.g., prions, virus, bacteria, etc.). Such information is critical for providing clinical diagnosis and prognosis.

A variety of methods are used for analysis of cells in various biological fluid samples. Methods for cellular analysis include visual and/or automated inspection via light or fluorescent light microscopy. Cellular examinations and analyses of these types are commonly practiced in order to obtain information regarding cell lineage, maturational stage, and/or cell counts in a sample.

Analysis of cells in a biological sample by microscopy can be expensive and time consuming. Flow cytometry provides an alternative method for identifying and distinguishing between different cell types and enumerating different cell types in a biological fluid sample. In the flow cytometer, cells are passed one at a time or nearly one at a time through a sensing region where each cell is irradiated by an energy source. Typically, single wavelength light sources (e.g., lasers, etc.) are used as the energy source and one or more of a variety of detectors record data based on the interaction of the cells with the applied energy. Flow cytometry is commonly used in hematology and has been successful in the diagnosis of blood diseases, including blood cancers.

Challenges in flow cytometry include capture of particle events (e.g., cell events) while removing undesirable signals (e.g., noise) that resemble small cell events. Other factors that adversely affect the quality of flow cytometry data include variation in nucleated cell counts from sample to sample, e.g., which results in variation in fluorescent signals such that the signals associated with cell events vary widely across different types of samples.

SUMMARY

Methods, devices, and systems for automated cellular analysis of a body fluid sample are disclosed. The methods, devices, and systems apply watershed transform to data, generated by flowing a body fluid sample through a flow cytometer, to determine threshold(s) to be used for analysis of the data.

In certain embodiments, a method for analyzing a body fluid containing cells is disclosed. The method may include collecting signals emitted by a body fluid sample irradiated by an energy source, where the body fluid sample is stained with a fluorescent dye, where the fluorescent dye permeates a cell membrane and binds to a nucleic acid to form a dye complex within the cell; applying a watershed transform to the collected signals thereby defining a plurality peaks and valleys in the collected signals; iteratively applying the watershed transform to the plurality peaks and valleys till a dominant valley is obtained; setting a threshold for signal analysis based on the signal of the dominant valley; and analyzing signals above the threshold to distinguish different types of cells in the body fluid. In certain embodiments, the body fluid sample is unlysed, i.e., the cells contained in the body fluid are unlysed.

In certain embodiments, the method may include iteratively applying the watershed transform to the plurality peaks and valleys till a dominant valley is obtained which dominant valley is positioned between two dominant peaks obtained by iteratively applying the watershed transform to the plurality of peaks.

In certain embodiments, the dominant valley may separate a first dominant peak corresponding to a first set of nucleated cell events from a second dominant peak corresponding to a second set of nucleated events.

In certain embodiments, the collected signals may include scattered light. The scattered light may include forward light scatter or side light scatter. The side light scatter may include polarized side scatter or depolarized side scatter. In certain embodiments, the collected signals may include fluorescent signal.

In certain embodiments, the method may include collecting a first plurality of signals that includes scattered light and a second plurality of signals that includes fluorescent signals; and (a) applying a watershed transform to the collected first plurality of signals thereby defining a plurality peaks and valleys; iteratively applying the watershed transform to the plurality peaks and valleys till a dominant valley is obtained; setting a threshold for analysis of the collected scattered light based on the signal of the dominant valley; and using the threshold to distinguish cellular events from non-cellular events; and (b) applying a watershed transform to the collected second plurality of signals thereby defining a plurality peaks and valleys; iteratively applying the watershed transform to the plurality peaks and valleys till a dominant valley is obtained; setting a threshold for analysis of the collected fluorescent signals based on the signal of the dominant valley; and using the threshold to distinguish nucleated cellular events from non-nucleated cellular events.

In certain embodiments, the method may include classifying nucleated cellular events into mononuclear cell events and non-white blood cell events.

In certain embodiments, step (b) may be carried out on fluorescent signals corresponding to cellular events identified in step (a).

In certain embodiments, the method may include classifying nucleated cellular events into mononuclear cell events, polymorphonuclear cell events, and non-white blood cell events. In certain embodiments, the method may include classifying mononuclear cell events into lymphocytes and monocyte/macrophages.

In certain embodiments, the body fluid may include blood, cerebrospinal fluid, pleural fluid, peritoneal fluid, pericardial fluid, synovial fluid, or continuous ambulatory peritoneal dialysis fluid. In certain embodiments, the method may include staining the body fluid sample with the fluorescent dye. In certain embodiments, the method may include flowing the stained body fluid sample through a flow cell of a hematology analyzer. In certain embodiments, the method may include irradiating the body fluid sample with the energy source.

Also disclosed herein is an automated system for analyzing cells in a body fluid. The system may include a computer including a memory for storing instructions for analyzing cells in a body fluid, the instructions being executed by a processor for collecting signals emitted by a body fluid sample irradiated by an energy source, wherein the body fluid sample is stained with a fluorescent dye, wherein the fluorescent dye permeates a cell membrane and binds to a nucleic acid to form a dye complex within the cell; applying a watershed transform to the collected signals thereby defining a plurality peaks and valleys in the collected signals; iteratively applying the watershed transform to the plurality peaks and valleys till a dominant valley is obtained; setting a threshold for signal analysis based on the signal of the dominant valley; and analyzing signals above the threshold to distinguish different types of cells in the body fluid.

The automated system may include a hematology analyzer including a flow cell; the energy source for irradiating the cells introduced into the flow cell; a plurality of detectors for detecting signals emitted by the cells in the flow cell, wherein the memory further comprises instructions for causing the hematology analyzer to stain the body fluid sample with the fluorescent dye; flow the stained body fluid sample through the flow cell; irradiate the cells flowing through the flow cell using the energy source.

In certain embodiments, the instructions may include instructions for iteratively applying the watershed transform to the plurality peaks and valleys till a dominant valley is obtained which dominant valley is positioned between two dominant peaks obtained by iteratively applying the watershed transform to the plurality peaks. In certain embodiments, the dominant valley may separate a first dominant peak corresponding to nucleated cell events from a second dominant peak corresponding to non-nucleated events.

The collected signals may include scattered light, such as, forward light scatter and/or side light scatter. The side light scatter may include polarized side scatter and/or depolarized side scatter. The collected signals may include fluorescent signal.

In certain embodiments, the instructions may include instructions for collecting a first plurality of signals comprising scattered light and a second plurality of signals comprising fluorescent signals; and: (a) applying a watershed transform to the collected first plurality of signals thereby defining a plurality peaks and valleys; iteratively applying the watershed transform to the plurality peaks and valleys till a dominant valley is obtained; setting a threshold for analysis of the collected scattered light based on the signal of the dominant valley; and using the threshold to distinguish cellular events from non-cellular events; and (b) applying a watershed transform to the collected second plurality of signals thereby defining a plurality peaks and valleys; iteratively applying the watershed transform to the plurality peaks and valleys till a dominant valley is obtained; setting a threshold for analysis of the collected fluorescent signals based on the signal of the dominant valley; and using the threshold to distinguish nucleated cellular events from non-nucleated cellular events. The instructions may include instructions for classifying nucleated cellular events into mononuclear cell events and non-white blood cell events. Step (b) may be carried out on fluorescent signals corresponding to cellular events identified in step (a).

In certain embodiments, the instructions may include instructions for classifying nucleated cellular events into mononuclear cell events, polymorphonuclear cell events, and non-white blood cell events. In certain embodiments, the instructions may include instructions for classifying mononuclear cell events into lymphocytes and monocyte/macrophages. The body fluid may be blood, cerebrospinal fluid, pleural fluid, peritoneal fluid, pericardial fluid, synovial fluid, or continuous ambulatory peritoneal dialysis fluid.

BRIEF DESCRIPTION OF THE FIGURES

FIG. 4A shows data for nucleated cells in pleural fluid. FIG. 4B shows data for nucleated cells in peritoneal fluid containing NWBCs.

FIG. 5A, RBCs (cells/µl); FIG. 5B, WBCs (cells/µl); FIG. 5C, mononuclear cell percentage (MN %); FIG. 5D, polymorphonuclear cell percentage (PMN %).

FIG. 7 is a schematic illustration of a second example of a flow cytometer according to one embodiment which finds use in generating data for analysis using the methods of the present disclosure.

DEFINITIONS

Figure 1A:
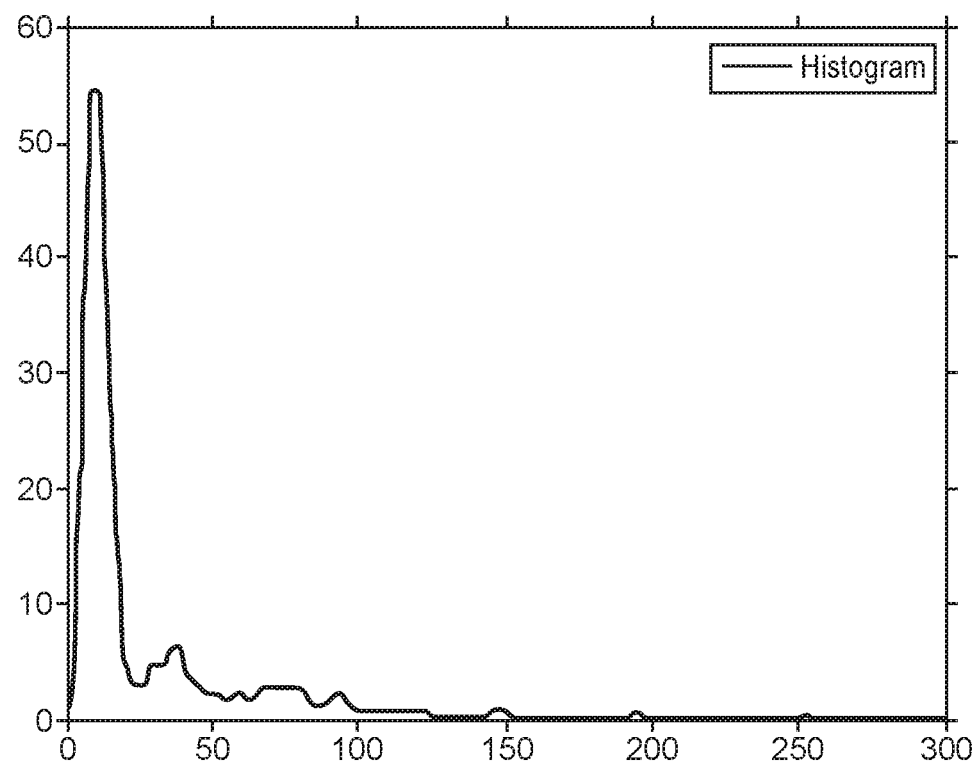
FIGS. 1A-1D provide an exemplary application of watershed transform to identify dominant peaks and valleys in one-dimensional signals.

The phrases "watershed transform" or "watershed algorithm" are used interchangeably and refer to the algorithm described in Luc Vincent and Pierre Soillie, Watersheds in digital spaces: an efficient algorithm based on immersion simulations. IEEE Transactions on Pattern Analysis and Machine Intelligence, 13 (6), 1991, pp. 583-598.

The term "bodily fluid" as used herein generally refers to fluids derived from a "biological sample" which encompasses a variety of sample types obtained from an individual or a population of individuals and can be used in a diagnostic, monitoring or screening assay. The definition encompasses blood and other liquid samples of biological origin. The definition also includes samples that have been manipulated in any way after their procurement, such as by mixing or pooling of individual samples, treatment with reagents, solubilization, or enrichment for certain components, such as nucleated cells, non-nucleated cells, pathogens, etc.

The term "biological sample" encompasses a clinical sample, and also includes cells in culture, cell supernatants, cell lysates, serum, plasma, biological fluid, and tissue samples. The term "biological sample" includes urine, saliva, cerebrospinal fluid (CSF), interstitial fluid, ocular fluid, synovial fluid, blood fractions such as plasma and serum, and the like.

By "data processing unit", as used herein, is meant any hardware and/or software combination that will perform the functions required of it. For example, any data processing unit herein may be a programmable digital processor (e.g., a microprocessor) such as available in the form of an electronic controller, mainframe, server, cloud, or personal computer (desktop or portable). Where the data processing unit is programmable, suitable programming can be communicated from a remote location to the data processing unit, or previously saved in a computer program product (such as a portable or fixed computer readable storage medium, whether magnetic, optical or solid state device based).

DETAILED DESCRIPTION

Methods, devices, and systems for automated cellular analysis of a body fluid sample are disclosed. The methods, devices, and systems apply watershed transform to data, generated by flowing a body fluid sample through a flow cytometer, to determine threshold(s) to be used for analysis of the data.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

Methods for analysis of body fluid samples are disclosed. These methods provide for an automated analysis of the types of cells present in a body fluid sample. These methods may be used in conjunction with an automated flow cytometer, such as, a hematology analyzer.

In certain embodiments, the methods disclosed herein may be used to identify a threshold used to analyze a body fluid sample. In certain embodiments, the method may include collecting signals emitted by a body fluid sample irradiated by an energy source, where the body fluid sample is stained with a fluorescent dye, where the fluorescent dye permeates a cell membrane and binds to a nucleic acid to form a dye complex within the cell; applying a watershed transform to the collected signals thereby defining a plurality peaks and valleys in the collected signals; iteratively applying the watershed transform to the plurality peaks and valleys till a dominant valley is obtained; setting a threshold for signal analysis based on the signal of the dominant valley; and analyzing signals above the threshold to identify different types of cells in the body fluid. In certain embodiments, the body fluid sample is unlysed, i.e., the cells contained in the body fluid are unlysed.

In certain embodiments, the method may include staining the body fluid sample with a fluorescent dye, where the fluorescent dye permeates a cell membrane and binds to a nucleic acid to form a dye complex within the cell. In certain embodiments, the method may also include flowing the stained body fluid sample through a flow cell of a flow cytometer, such as, a hematology analyzer, a fluorescence flow cytometer. The energy source for irradiating the flowing body fluid sample may be any suitable energy source, such as, a light source. In certain embodiments, the fluorescence flow cytometer may be configured as described in U.S. Pat. No. 5,631,165. The light source for irradiating the body fluid sample flowing through the flow cell may emit a laser beam. In certain embodiments, a standard argon ion laser may be used to irradiate the flowing body fluid sample.

The step of collecting signals emitted by a body fluid sample irradiated by an energy source may be carried out by a signal detection unit. The signal detection unit may be operatively coupled to a data processing unit. In some embodiments, the analysis of data collected by the signal detection unit may be performed by the data processing unit using the methods for data analysis provided herein.

The signal detection unit may include one signal detector or a plurality of signal detectors for detecting optical signals generated by optical interrogation of a body fluid sample flowing through a light beam in a flow cell of a flow cytometer (e.g., a hematology analyzer). Exemplary signal detectors include detectors for measuring optical signals such as, fluorescence signals, axial light loss (ALL, also known as forward extinction), intermediate Angle Scatter (IAS, light scattered at), small angle forward scattering (SAS), depolarized side scatter (DSS), and/or polarized side scatter (PSS). The collected signals may include one or more of fluorescence signals, ALL, IAS, SAS, DSS, and PSS.

ALL is generally the decrease in light energy due to a cell passing in front of a laser beam and being detected by a detector (e.g., a photodiode). The light loss is generally due to scattering and defined as the decrease in light energy reaching a detector in the path of a light beam (e.g., laser beam) due to the passage of a cell through that beam (generally ALL is detected at an angle of from about 0° to about 1°.) Small angle forward scatter (SAS), in contrast, is light energy that reaches a detector outside (but within a narrow angle of about 1° to 3°) the incident laser beam due to scattering from a cell passing through the beam. A beam stop is generally provided to keep the laser beam from getting into the detector. ALL measuring systems collect light within the incident cone of laser illumination, while small angle scatter systems collect light outside this cone. In ALL measuring systems, the signal of interest is a negative signal subtracted from the steady state laser signal, whereas in small angle forward scatter measurement the signal is a small positive signal imposed on a very low background light level. Intermediate angle forward scattering (IAS) is similar to small angle forward scattering, except the light is scattered at a larger angle from the incident laser beam. More specifically, IAS relates to light scattered in a ring between about 3° and 15° away from the incident or center line of a laser beam. In some embodiments, ALL is collected in the angles less than about 0.3° horizontally and less than about 1.2° vertically from the laser axis, and IAS is collected at angles between about 3° and 10° from the laser axis. In certain cases, DSS signals and PSS signals are measured at about 90° to the light beam incident in the flow cell.

The step of applying a watershed transform to the collected signals to define a plurality peaks and valleys in the collected signals may include organizing the collected signals into any format suitable for application of watershed transform algorithm. In certain embodiments, collected signals may be organized in a histogram format, a scattergram or other multidimensional plots. In certain aspects of the disclosed methods, the collected signals may include scattered light, such as side-scattered light, e.g., DSS and/or PSS and the intensity of scattered light may be plotted as a histogram. For example, the intensity of scattered light may be plotted over a period of time during which the body fluid sample is flowing through the flow cell. In certain embodiments, the intensity of scattered light may be plotted on the Y-axis and number of events (which may be cellular and non-cellular events) corresponding to the scattered light intensity may be plotted on X-axis, or vice versa. In certain embodiments, the X-axis may be different ranges of scattered light intensity (for example, divided into bins) and the Y-axis may be the number of events falling in the corresponding ranges of scattered light intensity. The intensity of scattered light measured for a cellular event (e.g., a blood cell) is higher than for a non-cellular event (e. g., cell debris such as RNA from lysed reticulocytes, Howell Jolly Bodies, reticulated platelets, giant platelets, DNA from white blood cells (WBCs) and Megakaryocytic fragments, parasites, red blood cell (RBC) fragment, red cell ghosts, aggregated proteins, etc.). Thus, applying the watershed transform to a two- or three-dimensional plot of the signals will define a plurality of peaks and a plurality of valleys in the signals. Some of the peaks, usually the less intense peaks, may correspond to signals from non-cellular events. However, without the use of watershed transform a data analysis system may apply a preset threshold value to distinguish cellular events from non-cellular events. However, this preset threshold value can vary depending upon the type of body fluid, the amount of dilution, the reagents used to prepare the body fluid sample for analysis, etc. Applying the watershed algorithm helps identify a custom threshold for the sample being analyzed taking into account the characteristics of the particular sample. The watershed algorithm is applied iteratively to the peaks and valleys identified initially till a single dominant valley remains. A threshold is chosen based on the signal of the dominant valley. The light scatter signals are then analyzed to distinguish cellular events from non-cellular events using the threshold as the cut-off, for example, scattered light of intensity higher than the threshold is counted as corresponding to a cellular event and scattered light of intensity lower than the threshold is counted as corresponding to a non-cellular event.

In certain embodiments, the iterative application of watershed transform includes merging a less dominant peak with a more dominant peak that is adjacent to the less dominant peak. In certain embodiments, the iterative application of watershed transform includes merging a less dominant valley with a more dominant valley that is adjacent to the less dominant valley. In certain embodiments, adjacent valleys or adjacent peaks that are merged may be merged when they are separated by less than a pre-defined distance. For example, the X-axis may have ranges of the signals that are separated by a certain intervals, such as, 1-10, >10-20, >20-30, >30-40, and so on. When a dominant valley corresponds to the 1-10 range and a less dominant valley corresponds to >10-20 range, these two valleys may be merged. The value of the merged valley may correspond to the value of the more dominant valley or may be an average of the two valleys. In certain embodiments, merging of a less dominant peak with a more dominant peak may be carried out in manner similar to merging of valleys. In certain embodiments, merging a less dominant valley with a more dominant valley may include removing the less dominant valley. Similarly, in certain embodiments, merging a less dominant peak with a more dominant peak may include removing the less dominant peak. Thus, in certain cases, iterative application of the watershed transform may include removing less dominant valleys till a single dominant valley remains. In certain embodiments, a less dominant valley may be a valley that is above a certain signal, which signal may be a predetermined signal, e.g., a signal known to be associated with a cellular event. In certain embodiments, a more dominant valley may be a valley that is below a certain signal, which signal may be a predetermined signal, e.g., a signal known to be associated with a non-cellular event. In certain embodiments, a less dominant peak may be a peak that is below a certain signal, which signal may be a predetermined signal, e.g., a signal known to be associated with a non-cellular event. In certain embodiments, a more dominant peak may be a peak that is above a certain signal, which signal may be a predetermined signal, e.g., a signal known to be associated with a cellular event. In other embodiments, a pre-determined signal is not used in determining dominant peaks and/or valleys, rather, the determination of dominant peaks and/or valleys is made de novo, e.g., on a sample-by-sample basis.

In another example, the collected signals may include fluorescent light signals. In certain embodiments, the intensity of fluorescent light signals may be plotted as a histogram. For example, the intensity of fluorescent light may be plotted over a period of time during which the body fluid sample is flowing through the flow cell. In certain embodiments, the intensity of fluorescent light may be plotted on the Y-axis and number of events (which may be nucleated cells and non-nucleated cells) corresponding to the fluorescence light intensity may be plotted on the X-axis, or vice versa. In certain embodiments, the X-axis may be ranges of intensity of fluorescent light (for example divided into bins) and Y-axis may be the number of events falling in the ranges plotted on the X-axis.

Figure 1B:
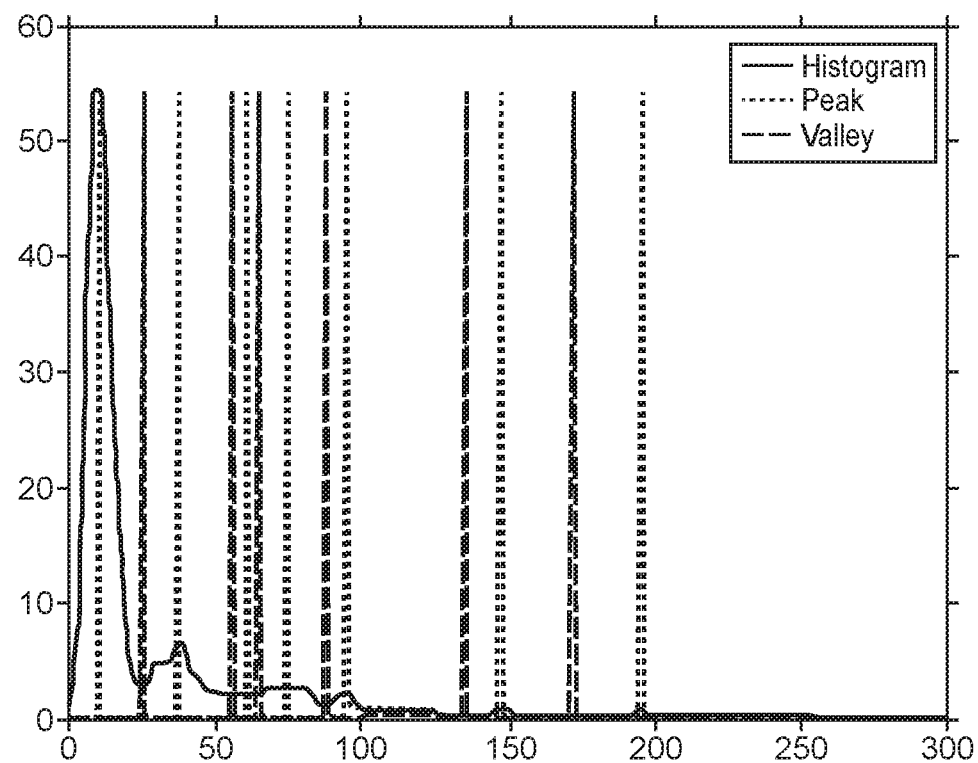
Figure 1C:
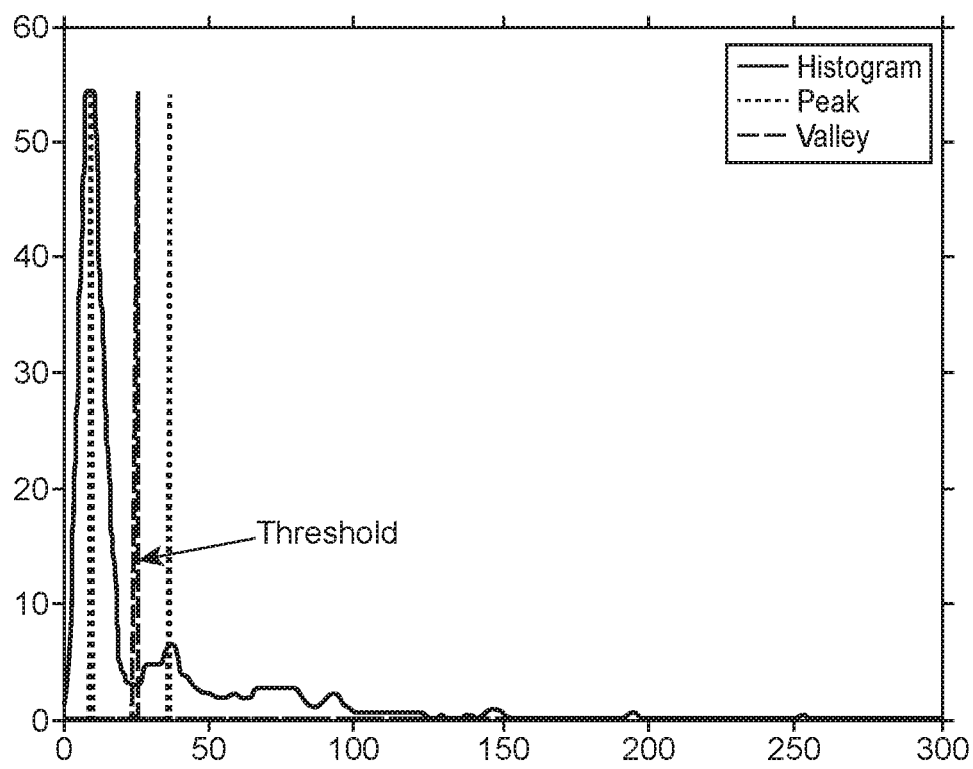

In another example, a graph may be generated displaying the frequency of the number of events associated with a particular signal intensity (e.g., fluorescence intensity or scattered light intensity). A theoretical histogram is displayed in FIG. 1A, the events associated with different light intensity (divided into different ranges or bins) are plotted on the X-axis and the frequency of occurrence of these events are plotted on the Y-axis. FIG. 1A shows that events associated with a certain light intensity are most frequent while other events are associated with different light intensities are less frequent. However, in order to identify which of the events associated with the different light intensities correspond to real events (e.g., cells—when the light signal is scattered light or nucleated cells—when the light signal is fluorescent light) and which correspond to non-events (e.g., cell debris—when the light signal is scattered light or non-nucleated cells—when the light signal is fluorescent light) a threshold needs to be utilized. As noted above, conventional threshold or gating approach, where a pre-determined threshold is utilized can introduce errors. The application of watershed transform is used here to identify a custom threshold for the data set being analyzed. FIG. 1B depicts the results from applying watershed transform to the raw data plotted in FIG. 1A. FIG. 1B shows that application of a watershed algorithm identifies a plurality of peaks and valleys. FIG. 1C depicts the end result of iteratively applying the watershed transform to the peaks and valleys identified in FIG. 1B. As shown in FIG. 1C, applying the watershed transform iteratively till a single dominant valley remains identifies the dominant valley as corresponding to a threshold that can be used for analyzing the data to distinguish events from non-events and provide an analysis of the body fluid sample.

Figure 1D:
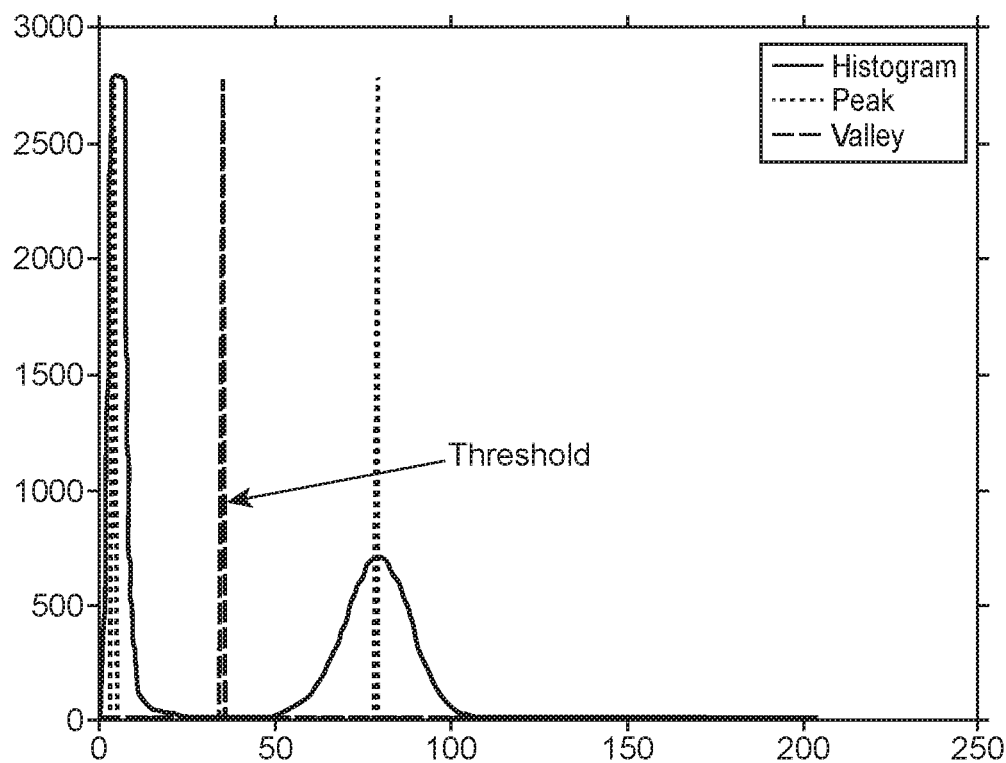

FIG. 1D provides results from the final iteration of applying watershed transform to another data set. Similar to the description for obtaining threshold for the data set in FIGS. 1A-1C, identification of peaks and valleys and iterative application of watershed transform to identify a dominant valley facilitates determination of a threshold specific to this data set. This threshold may then be used for analysis of the cells present in the body fluid sample from which the data set was generated.

In certain embodiments, iterative application of watershed transform to signals from a body fluid sample irradiated by an energy source, may be carried out till a desired outcome is achieved, for example, till a single dominant valley and/or a single dominant peak remains. In other embodiments, iterative application of watershed transform may be stopped when a single dominant valley and a plurality of dominant peaks (e.g., 2-10, 2-5, or 2-3, such as, 2, 3, 4, 5, 6, 7, 8, 9, or 10) remain. In another embodiment, iterative application of watershed transform may be stopped when a single dominant peak and a plurality of dominant valleys (e.g., 2-10, 2-5, or 2-3, such as, 2, 3, 4, 5, 6, 7, 8, 9, or 10) remain. In certain embodiments, the dominant valley may correspond to the threshold. In other embodiments, the dominant peak may correspond to the threshold.

In certain embodiments, each iteration of watershed algorithm may reduce the number of peaks and/or valleys compared to those obtained from a previous application of watershed algorithm. In some embodiments, the number of peaks and/or valleys may be reduced to identify dominant peaks and/or valleys by merging similar peaks and/or merging similar valleys, respectively. In addition or alternatively, to reducing the number of peaks and/or valleys to identify dominant peaks and/or valleys by merging similar peaks and/or merging similar valleys, respectively, less dominant peaks may be merged with a more dominant peak and a less dominant valley may be merged with a more dominant valley. As noted above, peaks separated by less than a pre-determined distance may be merged (e.g., a less dominant peak separated from a more dominant peak by less than a pre-determined distance may be removed and the more dominant peak retained). In some embodiments, the number of peaks and/or valleys may be reduced by removing peaks and/or valleys that correspond to signals predetermined to be artifacts or noise. In some embodiments, valleys that are not well separated from adjacent valley(s) may be merged with adjacent valley(s) or may be removed. A similar iteration may be performed with adjacent peaks.

In certain embodiments, the method includes iteratively applying the watershed transform to the plurality peaks and valleys till a dominant valley is obtained which dominant valley is positioned between two dominant peaks obtained by iteratively applying the watershed transform to the plurality of peaks.

In certain embodiments, iterative application of watershed transform to fluorescent signals obtained from the irradiated body fluid sample may identify a dominant valley separating a first dominant peak corresponding to a first plurality of nucleated cell events from a second dominant peak corresponding to a second plurality of nucleated events, where the dominant valley corresponds to the signals from the non-nucleated events. The first dominant peak may have a higher signal intensity than the second dominant peak and may correspond to signals generated from WBCs while the second dominant peal may correspond to signals generated from immature RBCs (reticulocytes). In certain embodiments, iterative application of watershed transform to scattered light recorded from the irradiated body fluid sample may identify a dominant valley separating a first dominant peak corresponding to a first plurality of bigger cells (e.g., WBCs) from a second dominant peak corresponding to a second plurality of smaller cells (e.g., platelets), where the dominant valley corresponds to the signals from the non-cellular events.

In certain embodiments, the method may include collecting a first plurality of signals comprising scattered light and a second plurality of signals comprising fluorescent light; and (a) applying a watershed transform to the collected first plurality of signals thereby defining a plurality peaks and valleys; iteratively applying the watershed transform to the plurality peaks and valleys till a dominant valley is obtained; setting a threshold for analysis of the collected scattered light based on the signal of the dominant valley; and using the threshold to distinguish cellular events from non-cellular events; and (b) applying a watershed transform to the collected second plurality of signals thereby defining a plurality peaks and valleys; iteratively applying the watershed transform to the plurality peaks and valleys till a dominant valley is obtained; setting a threshold for analysis of the collected fluorescent signals based on the signal of the dominant valley; and using the threshold to distinguish nucleated cellular events from non-nucleated cellular events.

In certain embodiments, step (a) and step (b) may be carried out simultaneously. In certain embodiments, step (a) and step (b) may be carried out sequentially in any order. In certain embodiments, step (b) may be carried out only on fluorescent signals corresponding to cellular events identified in step (a).

The method of the present disclosure may further include analyzing data corresponding to nucleated cellular events to identify the number of mononuclear cell events, polymorphonuclear cell events, and non-white blood cell events. The method may further include identifying the number of lymphocytes and monocyte/macrophages.

The body fluid sample that may be analyzed using the methods disclosed herein may include blood (e.g., a whole blood sample or fraction thereof), cerebrospinal fluid (CSF), pleural fluid, peritoneal fluid, pericardial fluid, synovial fluid, urine, saliva, tear, semen, amniotic fluid, sputum, continuous ambulatory peritoneal dialysis fluid (CAPD), and the like.

The body fluid sample may be processed before flowing through a flow cell of a hematology analyzer using any suitable protocol, such as, those described in U.S. Pat. Nos. 5,631,165 and 8,911,669, which are herein incorporated by reference in their entirety. For example, the body fluid sample may be stained with a fluorescent dye that permeates cell membrane and binds to a nucleic acid to form a dye complex within the cell. Any suitable dye that binds to DNA or RNA may be used. Some of the commercially available dyes that can be used include YOYO-1, YOYO-3, TOTO-1, TOTO-3, BO-PRO-1, YO-PRO-1, TO-PRO-1, and the like. It is known to those who are familiar in the art that the dyes with different Extinction (EX) max. can be excited with appropriate light source such as He—Ne, Xenon or Mercury lamps. In addition, the body fluid sample may optionally be exposed to isotonic solution and/or to other reagents for lysing RBCs. Further, the body fluid sample may optionally be exposed to a vital nuclear stain which effectively labels any nucleated (NRBC) which might be present in the body fluid being analyzed. The processed body fluid sample may optionally be diluted before flowing through a hematology analyzer.

The methods of the present disclosure may be used with other methods for accurate determination of patient counts which is the number of events per microliter of body fluid sample. The events may include red blood cells (RBCs), platelets (PLTs), white blood cells (WBCs), and classes or subclasses thereof. By "event" is meant the passing of a particle (e.g., a cell) through an interrogation zone of the flow cell, as detected by an optical interrogation system. By "non-event" or "non-cellular event" is meant optical signal features resembling an event which is not produced by an event. The methods of the present disclosure determine a threshold which can then be used to determine whether a signal is from an event or a non-event.

The raw signal data collected by the data collection unit may be analyzed using the methods disclosed herein. In other embodiments, the raw data may be processed before applying watershed transform. For example, the raw signal data may be filtered. Raw signal data may be filtered using an inverse Gaussian filter coefficient. Raw signal data may be processed to remove signals known to be noise (e.g., a particular flow cytometer may have a high background of baseline noise). Raw signal data may be digitized (e.g., analog signal may be converted into digital signal). Raw signal data or processed data may be further modified, e.g., converted to log scale, amplified, and the like. Raw signal data or processed data may be further formatted in any form suitable for applying watershed transform for identification of valleys and peaks.

Figure 2:
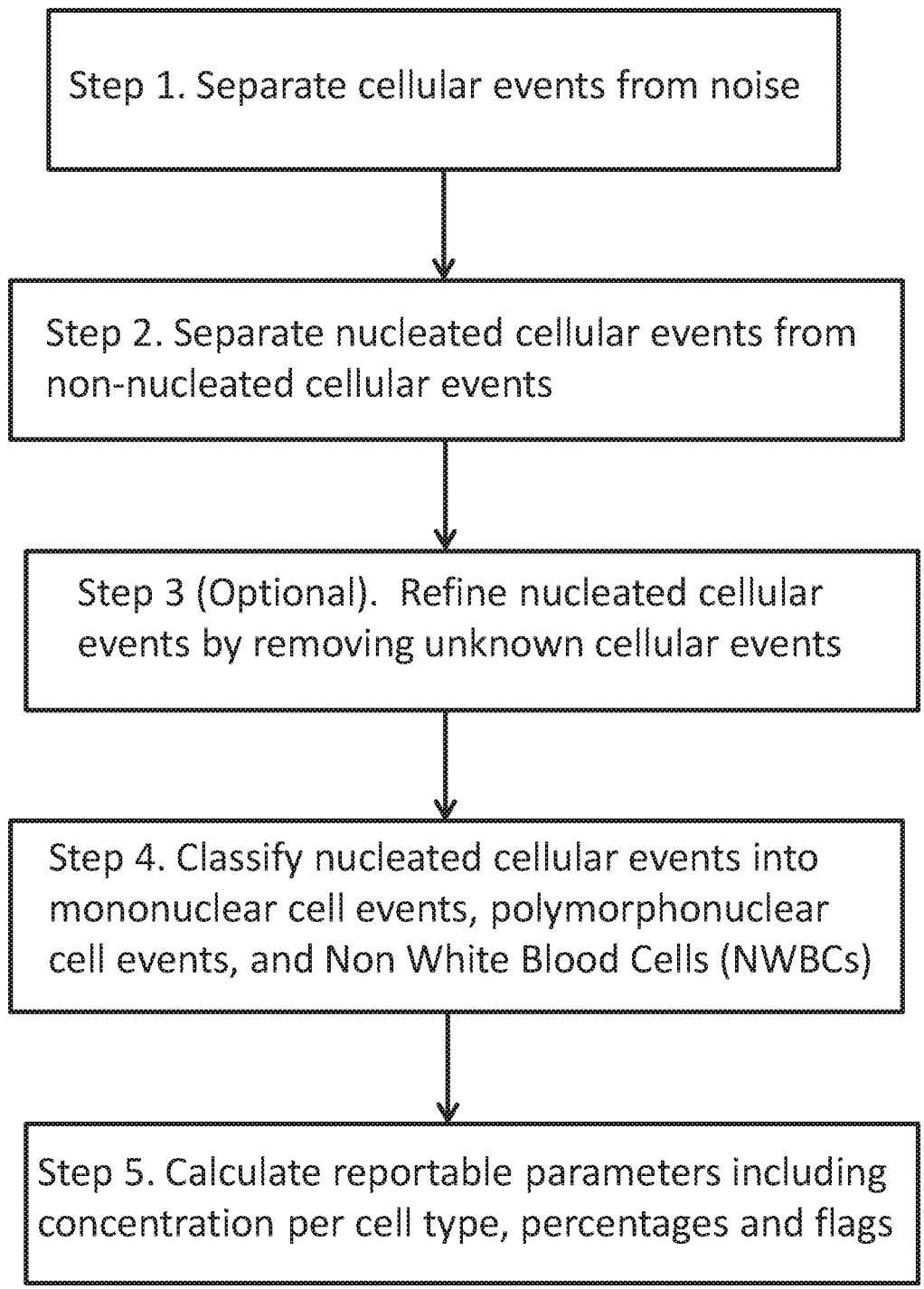
FIG. 2 is a flow chart depicting an exemplary method for body fluid analysis.

A certain embodiment of the methods disclosed herein is depicted in FIG. 2. FIG. 2 shows a flowchart showing steps for analyzing data collected from a body fluid sample using a hematology analyzer. Step 1 includes separating cellular events from noise based on their size scattering properties. After removing noise from the cellular events, the next step, Step 2, includes separating nucleated cell events from non-nucleated blood cells since nucleated cells emit stronger fluorescence signal upon staining with a fluorescent dye. Instead of a conventional threshold or gating approach, iterative watershed transform is utilized to automatically locate peaks and valleys along a histogram of the data. Watershed transform is initially applied to the signals to locate initial locations of peaks and valleys. Then an iterative procedure is applied to merge the less dominant peaks and valleys. Upon convergence of the procedure only the dominant peaks and valleys are left. The watershed transform is applied to data in Step 1 till only a dominant valley remains. The dominant valley is the cut-off threshold to separate different event types in Step 1. The watershed transform is applied to data in Step 2 till only a dominant valley remains. The dominant valley is the cut-off threshold to separate different event types in Step 2.

Figure 3:
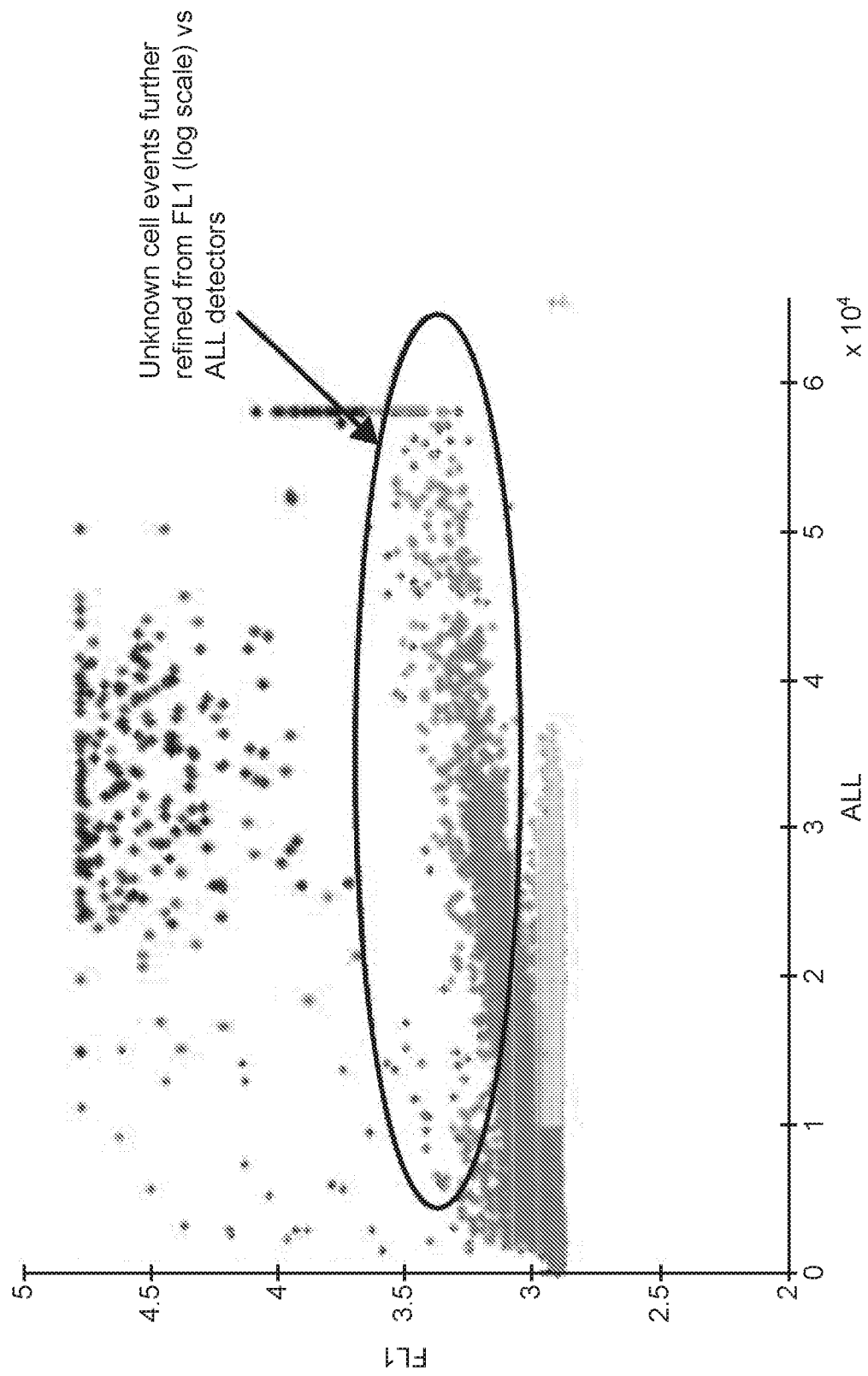
FIG. 3 is a scattergram of cerebrospinal (CSF) body fluid, where unknown events are refined from possible nucleated events (Step 3 of FIG. 2) in fluorescent light 1 (FL1) (log scale) vs. axial light loss (ALL).

FIG. 2, Step 3 is an optional step. In certain body fluid samples, additional unknown events forming additional cluster could be included in the nucleated cell events. A refinement approach as illustrated in FIG. 3 can be adopted to filter out the unknown events in order to achieve accurate total nucleated cell count (TNCC). In certain cases, the method for refining nucleated cellular events by removing unknown cell events (Step 3 in the flowchart) may utilize fluorescence signal and additional time stamp of the cell events with a non-parametric feature clustering technique (Mean Shift, Mode Seeking, and Clustering, IEEE Transactions on Pattern Analysis and Machine Intelligence, 17(8), 790-799, 1995).

Figure 4A:
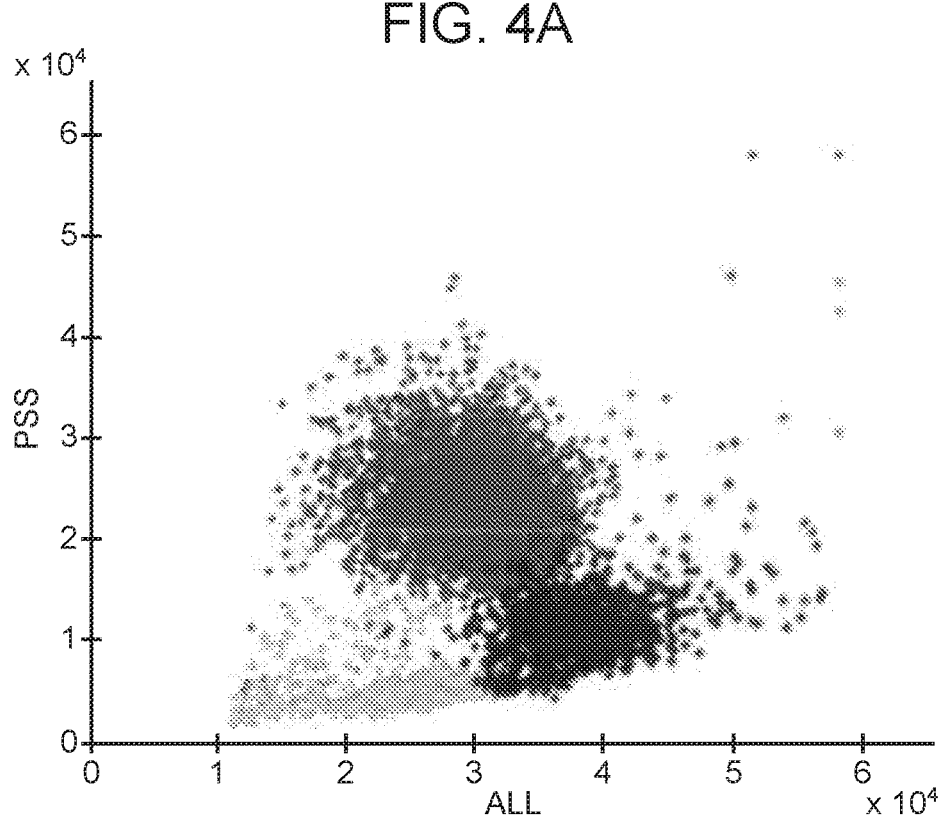
FIGS. 4A and 4B illustrate classification of nucleated cellular events into lymphocyte, monocytes/macrophages, polymorphonuclear (PMN) cell events, and non-white blood cells (NWBCs).
Figure 4B:
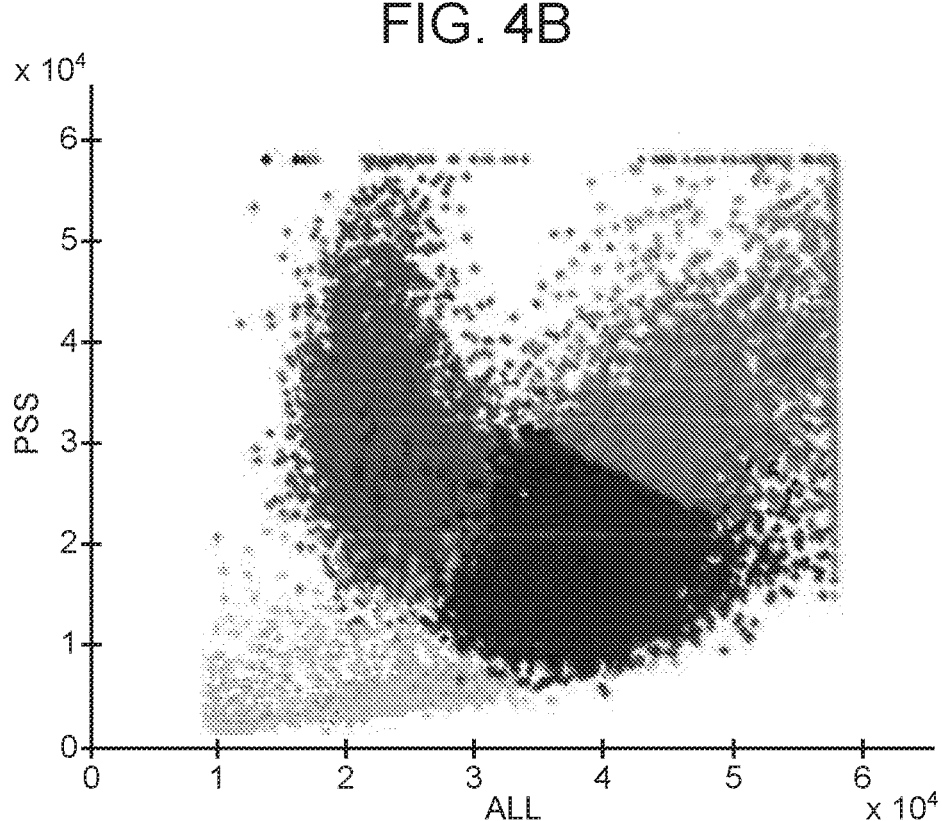
Figure 5B:
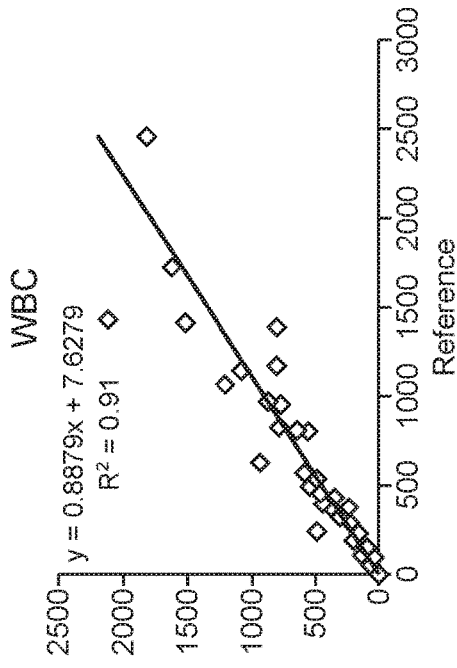
FIGS. 5A-5D illustrate correlation between cell counts obtained using a threshold identified from watershed transform as described herein and compared to a conventional method that uses a preset threshold.
Figure 5D:
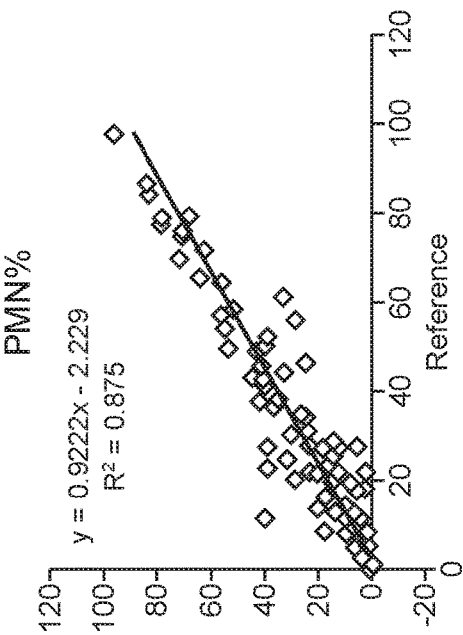
Figure 5A:
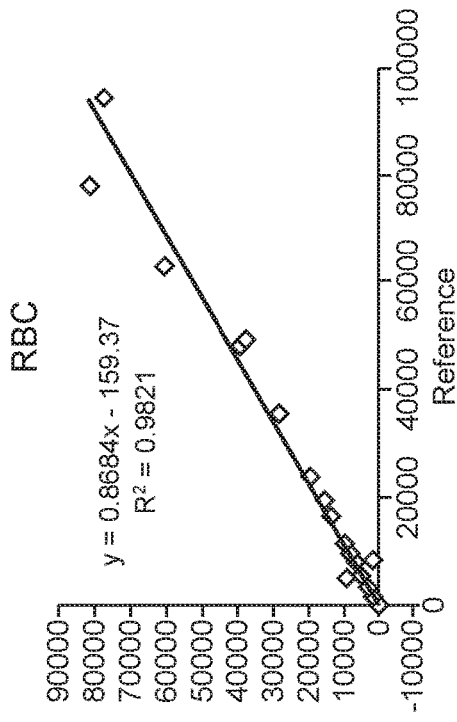
Figure 5C:
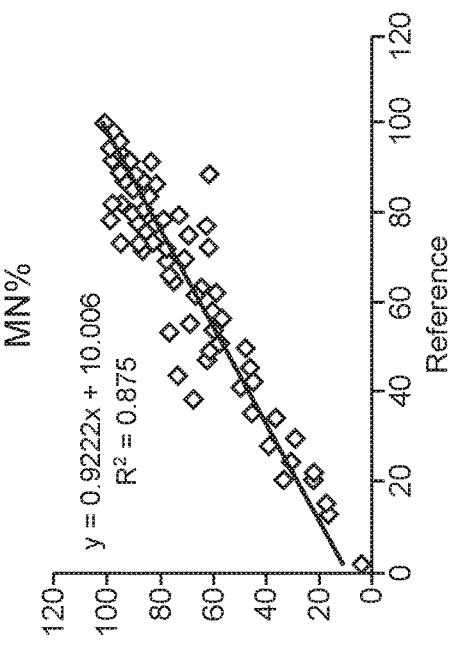

Step 4 of FIG. 2 includes classifying total nucleated cells into subcategories: lymphocytes, monocytes/macrophages, polymorphonuclear (PMN) cells, and NWBCs (NWBCs include nucleated cells that are not WBCs, NWBCs include epithelial cells and/or tumor cells). Lymphocytes and monocytes/macrophages can be enumerated as mononuclear cell (MNC) counts; WBCs include MNC and PMN cells. FIGS. 4A and 4B show two body fluid samples where TNCC are clustered into lymphocytes, monocytes/macrophage, PMN cells, and NWBCs. In certain embodiments, the method for classifying nucleated cellular events into mononuclear cell events, polymorphonuclear cell events, and non-white blood cell (NWBC) events (Step 4 in the flowchart) may utilize multiple dimensional light scattering signals (forward light scatter, side light scatter, polarized side scatter, depolarized side scatter, or a combination thereof) and fluorescence signals with an efficient k-means clustering algorithm (An efficient k-means clustering algorithm: analysis and implementation, IEEE Trans on Pattern Analysis and Machine Intelligence Vol. 24, 2002, 881-892).

FIG. 2, Step 5, the method further includes calculating reportable parameters including concentration per cell type, percentages and flags. In certain embodiments, the method for analysis of a body fluid sample may further includes providing a cell concentration based on dilution ratio, flow rate, counting time and appropriate calibration factors. Body fluid samples may be flagged to indicate further analysis, e.g., due to data quality and/or cell counts indicating potential malignancy. Flagged samples may be further analyzed using microscopy. Microscopy can be performed by a hematology analyzer having modules for preparing slides for the flagged samples and obtaining data from the slides using a microscope.

FIGS. 5A-5D demonstrate that analysis of a body fluid sample using the watershed transform to determine a threshold for data analysis provides cell counts that closely correlate to those derived using conventional methods utilizing pre-determined thresholds.

Classifying and enumerating total nucleated cells into subcategories: lymphocytes, monocytes/macrophages, polymorphonuclear (PMN) cells, and NWBCs may be carried out using any reliable method, such as, using the methods described in U.S. Pat. No. 5,631,165, incorporated herein by reference. One or more steps of the methods disclosed herein can be carried out in devices and systems described herein. Specific device and systems that perform aspects of the methods provided herein are described below in more detail below.

Devices and Systems

As summarized above, also provided by the present disclosure are devices and systems, e.g., which find use in practicing the methods of the present disclosure.

The devices used for practicing the methods disclosed herein may be a computer programmed to carry out one or more steps of the methods disclosed herein. The computer may include a memory for storing instructions for analyzing cells in a body fluid. The computer may also include a processor for executing the instructions stored in the memory. The instructions may include instructions for collecting signals emitted by a body fluid sample irradiated by an energy source, where the body fluid sample is stained with a fluorescent dye, where the fluorescent dye permeates a cell membrane and binds to a nucleic acid to form a dye complex within the cell; applying a watershed transform to the collected signals thereby defining a plurality peaks and valleys in the collected signals; iteratively applying the watershed transform to the plurality peaks and valleys till a dominant valley is obtained; setting a threshold for signal analysis based on the signal of the dominant valley; and analyzing signals above the threshold to distinguish different types of cells in the body fluid. As noted herein, the devices and systems described herein may be automated and thus may carry out the methods of the present disclosure without human intervention. Such devices and systems that carry out body fluid analysis by identifying a custom threshold for analyzing data generated from flowing the body fluid though a flow cytometer are improved over the devices and systems that use a preset threshold.

In certain embodiments, the above described computer may be part of flow cytometer, such as, a hematology analyzer, a fluorescence flow cytometer. The flow cytometer may include a flow cell, an energy source for irradiating cells introduced into the flow cell, where the memory of the flow cytometer may further include instructions for causing the flow analyzer to stain the body fluid sample with a fluorescent dye as described herein, flowing the stained body fluid sample through the flow cells, and irradiating the cells flowing through the flow cell.

In certain embodiments, the instructions may include instructions for iteratively applying the watershed transform to the plurality peaks and valleys till a dominant valley is obtained. The dominant valley is positioned between two dominant peaks obtained by iteratively applying the watershed transform to the plurality peaks.

Also provided by the present disclosure are systems (e.g., flow cytometry systems, which may be a subsystem of an automated hematology system) adapted to perform any of the methods of the present disclosure. Such systems may include any of the non-transitory computer-readable media described herein.

Figure 6:
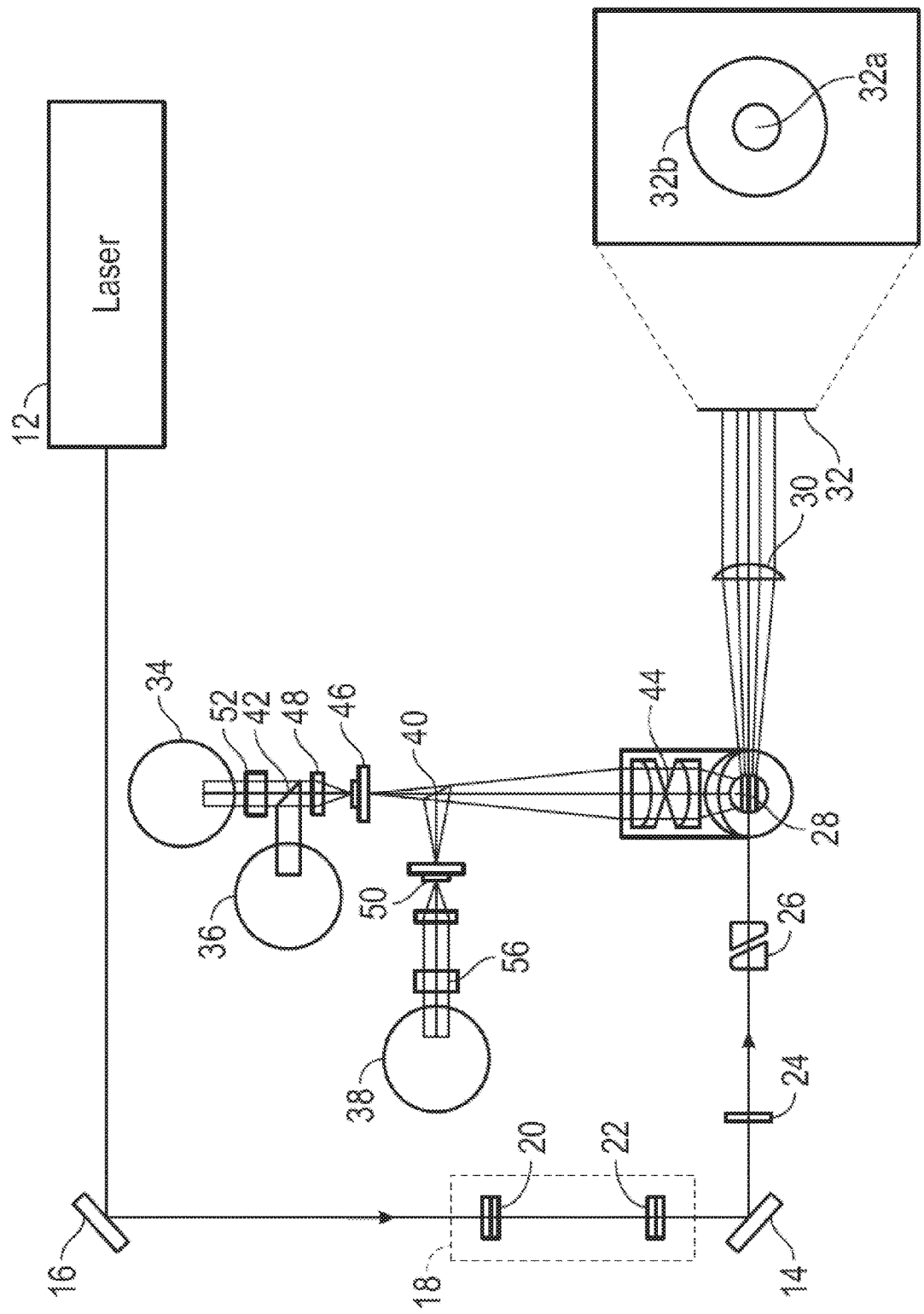
FIG. 6 is a schematic illustration of a first example of a flow cytometer according to one embodiment which finds use in generating data for analysis using the methods of the present disclosure.

In certain aspects, a system of the present disclosure is a flow cytometer. Such a system includes a flow cell, an excitation source positioned to excite a body fluid sample flowing through the flow cell, and one or more detectors for detecting optical signals emitted from the excited sample. An example of a flow cytometer which may include any of the herein-described non-transitory computer-readable media and suitable for practicing the methods of the present disclosure is schematically illustrated in FIG. 6. Flow cytometer 10 includes a source of light 12, a front mirror 14 and a rear mirror 16 for beam bending, a beam expander module 18 containing a first cylindrical lens 20 and a second cylindrical lens 22, a focusing lens 24, a fine beam adjuster 26, a flow cell 28, a forward scatter lens 30, a bulls-eye detector 32, a first photomultiplier tube 34, a second photomultiplier tube 36, and a third photomultiplier tube 38. The bulls-eye detector 32 has an inner detector 32a for 0° light scatter and an outer detector 32b for 7° light scatter.

In certain aspects, the source of light is a laser. However, other sources of light can be used, such as, for example, lamps (e.g., mercury, xenon). The source of light 12 can be a vertically polarized air-cooled Coherent Cube laser, commercially available from Coherent, Inc., Santa Clara, Calif. Lasers having wavelengths ranging from 350 nm to 700 nm can be used. Operating conditions for the laser are substantially similar to those of lasers currently used with "CELL-DYN" automated hematology analyzers.

Additional details relating to the flow cell, the lenses, the focusing lens, the fine-beam adjust mechanism and the laser focusing lens can be found in U.S. Pat. No. 5,631,165, incorporated herein by reference, particularly at column 41, line 32 through column 43, line 11. The forward optical path system shown in FIG. 2 of U.S. Pat. No. 5,631,165 includes a spherical plano-convex lens 30 and a two-element photodiode detector 32 located in the back focal plane of the lens. In this configuration, each point within the two-element photodiode detector 32 maps to a specific collection angle of light from cells moving through the flow cell 28. The detector 32 can be a bulls-eye detector capable of detecting axial light loss (ALL) and intermediate angle forward scatter (IAS). U.S. Pat. No. 5,631,165 describes various alternatives to this detector at column 43, lines 12-52.

A first photomultiplier tube 34 (PMT1) measures depolarized side scatter (DSS). The second photomultiplier tube 36 (PMT2) measures polarized side scatter (PSS), and the third photomultiplier tube 38 (PMT3) measures fluorescence emission from 440 nm to 680 nm, depending upon the fluorescent dye selected and the source of light employed. The photomultiplier tube collects fluorescent signals in a broad range of wavelengths in order to increase the strength of the signal. Side-scatter and fluorescent emissions are directed to these photomultiplier tubes by dichroic beam splitters 40 and 42, which transmit and reflect efficiently at the required wavelengths to enable efficient detection. U.S. Pat. No. 5,631,165 describes various additional details relating to the photomultiplier tubes at column 43, line 53 though column 44, line 4.

Sensitivity is enhanced at photomultiplier tubes 34, 36, and 38, when measuring fluorescence, by using an immersion collection system. The immersion collection system is one that optically couples the first lens 30 to the flow cell 28 by means of a refractive index matching layer, enabling collection of light over a wide angle. U.S. Pat. No. 5,631,165 describes various additional details of this optical system at column 44, lines 5-31.

The condenser 44 is an optical lens system with aberration correction sufficient for diffraction limited imaging used in high resolution microscopy. U.S. Pat. No. 5,631,165 describes various additional details of this optical system at column 44, lines 32-60.

The functions of other components shown in FIG. 6, i.e., a slit 46, a field lens 48, and a second slit 50, are described in U.S. Pat. No. 5,631,165, at column 44, line 63 through column 45, line 26. Optical filters 52 or 56 and a polarizer 52 or 56, which are inserted into the light paths of the photomultiplier tubes to change the wavelength or the polarization or both the wavelength and the polarization of the detected light, are also described in U.S. Pat. No. 5,631,165, at column 44, line 63 through column 45, line 26. Optical filters that are suitable for use herein include bandpass filters and long-pass filters.

The photomultiplier tubes 34, 36, and 38 detect either side-scatter (light scattered in a cone whose axis is approximately perpendicular to the incident laser beam) or fluorescence (light emitted from the cells at a different wavelength from that of the incident laser beam). FIG. 7 is a schematic illustration of a second example of a flow cytometer according to one embodiment which finds use in generating data for analysis using the methods of the present disclosure.

While select portions of U.S. Pat. No. 5,631,165 are referenced above, U.S. Pat. No. 5,631,165 is incorporated herein by reference in its entirety. According to certain embodiments, a flow cytometer of the present disclosure employs an Avalanche Photodiode (APD) as the photosensor.

In some instances, the components of the systems as described herein may be connected by a wired data connection. Any suitable and appropriate wired data connection may find use in connecting the components of the described systems, e.g., as described herein, including but not limited to e.g., commercially available cables such as a USB cable, a coaxial cable, a serial cable, a C2G or Cat2 cable, a Cat5/Cat5e/Cat6/Cat6a cable, a Token Ring Cable (Cat4), a VGA cable, a HDMI cable, a RCA cable, an optical fiber cable, and the like. In some instances, e.g., where data security is less of a concern, wireless data connections may be employed including but not limited to e.g., radio frequency connections (e.g., PAN/LAN/MAN/WAN wireless networking, UHF radio connections, etc.), an infrared data transmission connection, wireless optical data connections, and the like.

The devices and systems of the instant disclosure may further include a "memory" that is capable of storing information such that it is accessible and retrievable at a later date by a computer. Any convenient data storage structure may be chosen, based on the means used to access the stored information. In certain aspects, the information may be stored in a permanent memory (i.e., memory that is not erased by termination of the electrical supply to a computer or processor) or non-permanent memory. Computer harddrive, CD-ROM, floppy disk, portable flash drive and DVD are all examples of permanent memory. Random Access Memory (RAM) is an example of non-permanent memory. A file in permanent memory may be editable and re-writable.

Substantially any circuitry can be configured to a functional arrangement within the devices and systems for performing the methods disclosed herein. The hardware architecture of such circuitry, including e.g., a specifically configured computer, is well known by a person skilled in the art, and can comprise hardware components including one or more processors (CPU), a random-access memory (RAM), a read-only memory (ROM), an internal or external data storage medium (e.g., hard disk drive). Such circuitry can also comprise one or more graphic boards for processing and outputting graphical information to display means. The above components can be suitably interconnected via a bus within the circuitry, e.g., inside a specific-use computer. The circuitry can further comprise suitable interfaces for communicating with general-purpose external components such as a monitor, keyboard, mouse, network, etc. In some embodiments, the circuitry can be capable of parallel processing or can be part of a network configured for parallel or distributive computing to increase the processing power for the present methods and programs. In some embodiments, the program code read out from the storage medium can be written into a memory provided in an expanded board inserted in the circuitry, or an expanded unit connected to the circuitry, and a CPU or the like provided in the expanded board or expanded unit can actually perform a part or all of the operations according to the instructions of the programming, so as to accomplish the functions described.

In addition to the components of the devices and systems of the instant disclosure, e.g., as described above, systems of the disclosure may include a number of additional components, such as data output devices, e.g., monitors and/or speakers, data input devices, e.g., interface ports, keyboards, etc., actuatable components, power sources, etc.

Computer Readable Media

As summarized above, also provided by the present disclosure are computer-readable media, e.g., which find use in practicing the methods of the present disclosure.

The instant disclosure includes computer readable medium, including non-transitory computer readable medium, which stores instructions for methods described herein. Aspects of the instant disclosure include computer readable medium storing instructions that, when executed by a computing device (e.g., processor of a computing device), cause the computing device to perform one or more steps of a method as described herein. According to certain embodiments, a computer readable medium may include instructions for collecting signals emitted by a body fluid sample irradiated by an energy source, where the body fluid sample is stained with a fluorescent dye, where the fluorescent dye permeates a cell membrane and binds to a nucleic acid to form a dye complex within the cell; applying a watershed transform to the collected signals thereby defining a plurality peaks and valleys in the collected signals; iteratively applying the watershed transform to the plurality peaks and valleys till a dominant valley is obtained; setting a threshold for signal analysis based on the signal of the dominant valley; and analyzing signals above the threshold to distinguish different types of cells in the body fluid. As noted herein, the devices and systems described herein may be automated and thus may carry out the methods of the present disclosure without human intervention.

In certain embodiments, instructions in accordance with the methods described herein can be coded onto a computer-readable medium in the form of "programming", where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programming that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A computer implemented method for analyzing a body fluid containing cells, the method comprising:
    collecting signals emitted by a body fluid sample irradiated by an energy source, wherein the body fluid sample is stained with a fluorescent dye, wherein the fluorescent dye permeates a cell membrane and binds to a nucleic acid to form a dye complex within the cell;
    applying a watershed transform to the collected signals thereby defining a plurality peaks and valleys in the collected signals;
    iteratively applying the watershed transform to the plurality peaks and valleys, including, in each iteration, merging a less dominant one of the valleys with a more dominant one of the valleys that is adjacent to the less dominant valley and separated by less than a predetermined distance or merging a less dominant one of the peaks with a more dominant one of the peaks that is adjacent to the less dominant peak and separated by a predetermined distance, the method including iterating until a dominant valley is obtained;
    setting a threshold for signal analysis based on the signal of the dominant valley; and
    analyzing signals above the threshold to distinguish different types of cells in the body fluid.

2. The computer implemented method of claim 1, wherein the method comprises iteratively applying the watershed transform to the plurality peaks and valleys till a dominant valley is obtained which dominant valley is positioned between two dominant peaks obtained by iteratively applying the watershed transform to the plurality of peaks.

3. The computer implemented method of claim 1, wherein dominant valley separates a first dominant peak corresponding to a first set of nucleated cell events from a second dominant peak corresponding to a second set of nucleated events.

4. The computer implemented method of claim 1, wherein the collected signals comprise scattered light.

5. The computer implemented method of claim 4, wherein the scattered light comprises forward light scatter.

6. The computer implemented method of claim 4, wherein the scattered light comprises side light scatter.

7. The computer implemented method of claim 6, wherein the side light scatter comprises polarized side scatter.

8. The computer implemented method of claim 6, wherein the side light scatter comprises depolarized side scatter.

9. The computer implemented method of claim 1, wherein the collected signals comprise fluorescent signal.

10. The computer implemented method of claim 1, wherein the method comprises collecting a first plurality of signals comprising scattered light and a second plurality of signals comprising fluorescent signals; and:
    (a) applying a watershed transform to the collected first plurality of signals thereby defining a plurality peaks and valleys; iteratively applying the watershed transform to the plurality peaks and valleys till a dominant valley is obtained; setting a threshold for analysis of the collected scattered light based on the signal of the dominant valley; and using the threshold to distinguish cellular events from non-cellular events; and
    (b) applying a watershed transform to the collected second plurality of signals thereby defining a plurality peaks and valleys; iteratively applying the watershed transform to the plurality peaks and valleys till a dominant valley is obtained; setting a threshold for analysis of the collected fluorescent signals based on the signal of the dominant valley; and using the threshold to distinguish nucleated cellular events from non-nucleated cellular events.

11. The computer implemented method of claim 1, further comprising classifying nucleated cellular events into mononuclear cell events and non-white blood cell events.

12. The computer implemented method of claim 10, wherein step (b) is carried out on fluorescent signals corresponding to cellular events identified in step (a).

13. The computer implemented method of claim 12, further comprising classifying nucleated cellular events into mononuclear cell events, polymorphonuclear cell events, and non-white blood cell events.

14. The computer implemented method of claim 13, further comprising classifying mononuclear cell events into lymphocytes and monocyte/macrophages.

15. The computer implemented method of claim 1, wherein the body fluid comprises blood, cerebrospinal fluid, pleural fluid, peritoneal fluid, pericardial fluid, synovial fluid, or continuous ambulatory peritoneal dialysis fluid.

16. The computer implemented method of claim 1, comprising staining the body fluid sample with the fluorescent dye.

17. The computer implemented method of claim 16, comprising flowing the stained body fluid sample through a flow cell of a hematology analyzer.

18. The computer implemented method of claim 17, comprising irradiating the body fluid sample with the energy source.

19. An automated system for analyzing cells in a body fluid, the system comprising:
a computer comprising:
a memory for storing instructions for analyzing cells in a body fluid, the instructions being executed by a processor for:
collecting signals emitted by a body fluid sample irradiated by an energy source, wherein the body fluid sample is stained with a fluorescent dye, wherein the fluorescent dye permeates a cell membrane and binds to a nucleic acid to form a dye complex within the cell;
applying a watershed transform to the collected signals thereby defining a plurality peaks and valleys in the collected signals;
iteratively applying the watershed transform to the plurality peaks and valleys, including, in each iteration, merging a less dominant one of the valleys with a more dominant one of the valleys that is adjacent to the less dominant valley and separated by less than a predetermined distance or merging a less dominant one of the peaks with a more dominant one of the peaks that is adjacent to the less dominant peak and separated by a predetermined distance, the method including iterating until a dominant valley is obtained;
setting a threshold for signal analysis based on the signal of the dominant valley; and
analyzing signals above the threshold to distinguish different types of cells in the body fluid.

20. The automated system of claim 19, further comprising a hematology analyzer comprising:
a flow cell;
the energy source for irradiating the cells introduced into the flow cell;
a plurality of detectors for detecting signals emitted by the cells in the flow cell,
wherein the memory further comprises instructions for causing the hematology analyzer to:
stain the body fluid sample with the fluorescent dye;
flow the stained body fluid sample through the flow cell;
irradiate the cells flowing through the flow cell using the energy source.

21. The automated system of claim 19, wherein the instructions comprise instructions for iteratively applying the watershed transform to the plurality peaks and valleys till a dominant valley is obtained which dominant valley is positioned between two dominant peaks obtained by iteratively applying the watershed transform to the plurality peaks.

22. The automated system of claim 19, wherein the dominant valley separates a first dominant peak corresponding to nucleated cell events from a second dominant peak corresponding to non-nucleated events.

23. The automated system of claim 19, wherein the collected signals comprise scattered light.

24. The automated system of claim 23, wherein the scattered light comprises forward light scatter.

25. The automated system of claim 23, wherein the scattered light comprises side light scatter.

26. The automated system of claim 25, wherein the side light scatter comprises polarized side scatter.

27. The automated system of claim 25, wherein the side light scatter comprises depolarized side scatter.

28. The automated system of claim 19, wherein the collected signals comprise fluorescent signal.

29. The automated system of claim 19, wherein the instructions comprise instructions for collecting a first plurality of signals comprising scattered light and a second plurality of signals comprising fluorescent signals; and:
(a) applying a watershed transform to the collected first plurality of signals thereby defining a plurality peaks and valleys; iteratively applying the watershed transform to the plurality peaks and valleys till a dominant valley is obtained; setting a threshold for analysis of the collected scattered light based on the signal of the dominant valley; and using the threshold to distinguish cellular events from non-cellular events; and
(b) applying a watershed transform to the collected second plurality of signals thereby defining a plurality peaks and valleys; iteratively applying the watershed transform to the plurality peaks and valleys till a dominant valley is obtained; setting a threshold for analysis of the collected fluorescent signals based on the signal of the dominant valley; and using the threshold to distinguish nucleated cellular events from non-nucleated cellular events.

30. The automated system of claim 29, the instructions comprising instructions for classifying nucleated cellular events into mononuclear cell events and non-white blood cell events.

31. The automated system of claim 29, wherein step (b) is carried out on fluorescent signals corresponding to cellular events identified in step (a).

32. The automated system of claim 31, the instructions comprising instructions for classifying nucleated cellular events into mononuclear cell events, polymorphonuclear cell events, and non-white blood cell events.

33. The automated system of claim 32, further comprising classifying mononuclear cell events into lymphocytes and monocyte/macrophages.

34. The automated system of claim 19, wherein the body fluid comprises a blood, cerebrospinal fluid, pleural fluid, peritoneal fluid, pericardial fluid, synovial fluid, or continuous ambulatory peritoneal dialysis fluid.

* * * * *